United States Patent [19]

Greene et al.

[11] Patent Number: 4,477,594

[45] Date of Patent: Oct. 16, 1984

[54] PROCESS FOR THE SYNTHESIS OF ALIPHATIC ALCOHOL-CONTAINING MIXTURES

[75] Inventors: Marvin I. Greene, Oradell; Abraham P. Gelbein, Morristown, both of N.J.

[73] Assignee: Chem Systems, Inc., Tarrytown, N.Y.

[21] Appl. No.: 450,341

[22] Filed: Dec. 16, 1982

[51] Int. Cl.$^3$ .................... C07C 27/06; C07C 31/00
[52] U.S. Cl. ................................ 518/700; 518/713
[58] Field of Search ........................... 518/700, 713

[56] References Cited

U.S. PATENT DOCUMENTS 3,888,896  6/1975  Espino et al. .................. 518/713
4,031,123  6/1977  Espino et al. .................. 518/713

FOREIGN PATENT DOCUMENTS 5492  11/1979  European Pat. Off. ............ 518/713
3005551  8/1981  Fed. Rep. of Germany ...... 518/713

OTHER PUBLICATIONS

Sherwin et al., Liquid Phase Methanol, AF-693, Research Project, 317-2, Prepared by Chem. Systems, (1978), pp. iii, 2-2.

*Primary Examiner*—Howard T. Mars
*Attorney, Agent, or Firm*—Bert J. Lewen; Marvin Bressler

[57] ABSTRACT

A process for the synthesis of mixtures which include saturated aliphatic alcohols is disclosed. In the first step of the process, the first catalyst activation stage, a catalyst, which comprises the oxides of copper, zinc, aluminum, potassium and one or two additional metals selected from the group consisting of chromium, magnesium, cerium, cobalt, thorium and lanthanum, is partially activated. In this step, a reducing gas stream, which includes hydrogen and at least one inert gas, flows past the catalyst at a space velocity of up to 5,000 liters (STP) per hour, per kilogram of catalyst. The partially activated catalyst is then subjected to the second step of the process, second-stage catalyst activation. In this step, the catalyst is contacted by an activation gas stream comprising hydrogen and carbon monoxide present in a volume ratio of 0.5:1 and 4:1, respectively, at a temperature of 200° to 450° C. and a pressure of between 35 and 200 atmospheres. The activation gas flows at a space velocity of from 1,000 to 20,000 liters (STP) per hour, per kilogram of catalyst. Second-stage activation continues until the catalyst is contacted with at least 500,000 liters (STP) of activation gas per kilogram of catalyst. The fully activated catalyst, in the third step of the process, contacts a synthesis gas stream comprising hydrogen and carbon monoxide.

25 Claims, No Drawings

PROCESS FOR THE SYNTHESIS OF ALIPHATIC ALCOHOL-CONTAINING MIXTURES

The U.S. Government has rights in this invention pursuant to Contract No. DE-AC22-79 ET14858 awarded by the United States Department of Energy.

BACKGROUND OF THE DISCLOSURE

1. Field of the Invention

The instant invention is directed to a process for the synthesis of mixtures including aliphatic alcohols. More specifically, the instant invention is directed to a process for the synthesis of low boiling $C_1$ to $C_9$ aliphatic alcohol-containing mixtures from hydrogen and carbon monoxide.

2. Background of the Prior Art

The synthesis of methanol from carbon monoxide and hydrogen by the metal catalyzed Fischer-Tropsch process has long been known in the art. This process has enjoyed a revitalization what with the development of alcohol and so called gasohol fuels. A key reason for this new interest in the use of alcohol-gasoline fuel mixtures, in addition to the obvious conservation of liquid petroleum, is the fact that alcohol in alcohol-gasoline or gasohol fuels generally have more favorable anti-knock qualities than do gasolines. This tends to raise the octane number of gasohol mixtures compared to straight gasoline.

Recent studies of alcohol based fuels have indicated that even more satisfactory results are obtainable with the use of higher aliphatic alcohols alone or in admixture with methanol and higher aliphatic alcohols. The referred to studies indicate that when a mixture of methanol and $C_2$–$C_9$ saturated alcohols is used as a blend with gasoline, such fuel is found superior to gasohol, that is, the combination of gasoline and methanol or gasoline with methanol and ethanol, fuels presently known in the art.

Among the advantages of fuels incorporating aliphatic alcohols is reduced elevation in fuel blend vapor pressure compared to the presently employed gasohol. Increase in the vapor pressure of fuel blends results in vapor lock problems. This volatility problem, inherent in the use of methanol, decreases the drivability of such a fuel blend. On the other hand, a mixture of higher alcohols have a lower vapor pressure than methanol with a resultant decrease in vapor lock and improved drivability.

A requirement of alcohol-gasoline blends is their homogeneity. The alcohol and the gasoline must not separate into separate phases. It has been found that methanol is less soluble in the average gasoline than is a mixture of higher alcohols.

Another physical property of alcohol-gasoline blends, water tolerance, relates also to the prevention of phase separation. A low water tolerance results in the formation of two phases, an upper gasoline-rich phase and a lower alcohol-rich phase. This separation, a function of the amount of water in the two phases, can have highly undesirable effects such as corrosion of automobile fuel system components, engine stall and the like. It has been found that of all aliphatic alcohols methanol has the lowest water tolerance. $C_2$–$C_9$ mixtures, which act as co-solvents for methanol, significantly improve the water tolerance of methanol by as much as 500%.

The above remarks emphasize the potential for gasoline-alcohol fuel blends wherein the alcohol constituent is a combination of methanol and higher aliphatic alcohols. However, the synthesis processes of the prior art result in the formation of methanol only or alcohol blends in which methanol predominates. There has been little disclosure in the prior art of processes in which higher alcohols, i.e., $C_2$–$C_9$, are produced in sufficient amount to provide the necessary volume of higher alcohols for use in alcohol-gasoline fuel blends.

Among the more recent disclosures directed to processes for synthesizing mixtures of methanol and higher alcohols is U.S. Pat. No. 4,122,110 issued to Sugier et al. This patent discloses the formation of such a blend of alcohol from synthesis gas. The process of the Sugier et al patent is catalyzed by a catalyst which comprises at least four essential elements, copper, cobalt, a third metal selected from chromium, iron, vanadium and manganese and at least one alkali metal, preferably lithium, sodium or potassium. In this process, it is preferred to add an organic complexant to a common solution of the copper, cobalt and a third metal catalyst which, the reference teaches, results in a catalyst of higher selectivity.

Another recent disclosure directed to the synthesis of mixtures of methanol and higher alcohols is U.K. Patent Application GB No. 2,083,469 A. In this application, a process is recited in which a synthesis gas, containing hydrogen and carbon monoxide, is reacted in the presence of a catalyst based on chromium, zinc and at least one alkali metal.

Yet another recent publication, German OLS No. 3005551 A1, discloses a catalyst for the synthesis of methanol and higher alcohol mixtures. Although the catalyst of the '551 disclosure is used in the present invention, there is no disclosure in the application of a process for producing a satisfactory methanol-higher alcohol product mixture.

Still another recent reference, UK Patent Application GB No. 2,087,749A, discloses the synthesis of hydrocarbons, e.g., methane or alcohols, e.g., methanol, from a CO—$H_2$ gas reactant feed in which the gas phase reactants contact a fixed bed catalyst while diluted with an inert liquid phase material.

BRIEF SUMMARY OF THE INVENTION

The instant invention is directed to a process for the synthesis of aliphatic alcohols in which the ratio of higher alcohols to methanol is sufficiently high to produce a satisfactory composition for the blending of the alcohol with gasoline to produce an excellent gasohol product.

In accordance with the instant invention a process is provided for the synthesis of mixtures including aliphatic alcohols. The process incorporates a three step procedure of which first stage activation is the first. In the first stage activation step a reducing gas stream comprising hydrogen and at least one inert gas is exposed to a catalyst, said catalyst comprising the oxides of copper, zinc, aluminum, potassium and one or two metals selected from the group consisting of chromium, manganese, cerium, cobalt, thorium and lanthanum. The first stage activation step is characterized by a reducing gas space velocity of up to 5000 liters of gas at standard temperature and pressure (STP) per hour per kilogram of catalyst. The duration of said first stage activation is measured by the time necessary to raise the temperature in the first stage activation reactor to a maximum temperature from ambient temperature at the start of activation wherein the maximum increase in temperature is 25° C. per hour. The maximum temperature is in the range of between 200° and 450° C.

The second step in the process of this invention is the second stage activation step. In this step the catalyst, after first stage activation, is exposed to an activation gas stream comprising hydrogen and carbon monoxide, present in a volume ratio in the range of between 0.5:1 and 4:1 respectively, at a temperature in the range of between 200° and 450° C. and a pressure in the range of between 35 and 200 atmospheres. The second stage activation step continues until at least 500,000 liters of activation (at STP) gas per kg of catalyst has contacted the catalyst. The activation gas space velocity in second stage activation is in the range of between 1,000 and 20,000 liters (at STP) of activation gas per hour per kilogram of catalyst.

The third and final step in the process is the synthesis step wherein a synthesis gas stream having the same composition as the activation gas stream is exposed to the activated catalyst at a temperature in the range of between 200° C. and 450° C. and a pressure in the range of between 35 and 300 atmospheres to produce the aliphatic alcohol containing mixture of this invention.

DETAILED DESCRIPTION

The process of this invention begins with the activation of a catalyst, later used to catalyze the reaction to produce a mixture of aliphatic alcohols. The catalyst of this invention, activated in the first and second steps of the process of this invention, is a mixture of the oxides of copper, zinc, aluminum, potassium and one or two metals selected from the group consisting of chromium, manganese, cerium, cobalt, thorium and lanthanum. The concentrations of these metal oxides comprising the catalyst of this invention, expressed as a percentage by weight of the free metal based on the total free metal weight of the catalyst, are as follows: copper, 18 to 25 percent; zinc, 24 to 50 percent; aluminum, 5 to 25 percent; potassium, 1.4 to 2.1 percent; and the fifth and optionally the sixth metal, 2.1 to 12.5 percent. The catalyst is furthermore characterized by a copper to zinc weight ratio in the range of between 0.4:1 and 1.9:1. In a preferred embodiment the additional metal constituents are selected from the group consisting of chromium, manganese and both of them.

The first stage activation step comprises the first of two steps in the activation of the above described catalyst. The activation is initiated by exposing said catalyst to a stream of a reducing gas. The reducing gas includes hydrogen, present in a molar concentration of between 1 and 98 percent. The remainder of the reducing gas stream is inert gases of which nitrogen is preferred. Other inert gases, with or without nitrogen, may be included in the reducing gas of the first activation stage.

The first stage activation step encompasses a reaction in which the catalyst is activated by partial reduction of the metal oxides of the catalyst of this invention by the reducing gas stream. To effect this reduction the reducing gas contacts the catalyst at a space velocity of up to 5000 liters, measured at 0° C. and 1 atmosphere, i.e., STP, of reducing gas per hour per kilogram of catalyst. It is preferred that the minimum space velocity be 200 liters (STP) per hour per kilogram of catalyst. The duration of this contact is the time necessary to raise the temperature in the reactor from ambient to a maximum temperature in the range of between 200° and 450° C. with the limitation that the temperature not rise by more than 25° C. per hour. The pressure in the reactor during first stage activation is in the range of between 1 and 15 atmospheres, more preferably between 1 and 10 atmospheres, and most preferably, between 1 and 5 atmospheres. The first stage activation is furthermore characterized by a rate of conversion of hydrogen in the reducing gas stream in the range of between 15 and 95 percent, more preferably, between 20 and 75 percent, per pass through the first activation stage reactor.

Upon completion of first stage activation, second stage activation is initiated. In this stage, an activation gas stream comprising hydrogen and carbon monoxide contacts the catalyst to complete the activation of said catalyst.

The activation gas stream is characterized by a hydrogen to carbon monoxide volume ratio in the range of between 0.5:1 and 4:1. More preferably, this volume ratio is between 2:1 and 2.5:1. The activation gas also includes diluent gases present in a concentration in the range of between 1 and 15 percent by volume, more preferably, 1 to 5 volume percent, based on the total volume of the activation gas. Diluent gas, within the contemplation of this invention, includes one or more of nitrogen, methane, methanol, ethane, ethanol and propane. Finally, the activation gas may further comprise carbon dioxide in a concentration of 0 to 25 volume percent, again, based on the total volume of the activation gas. More preferably, the carbon dioxide concentration is between 0.1 and 2 volume percent. If present, the partial pressure of the carbon dioxide is less than 13 atmospheres, more preferably, less than 5 atmospheres.

The second stage activation step takes place in a reactor maintained at a constant temperature in the range of between 200° and 450° C., more preferably, between 275° and 425° C. and most preferably between 300° and 400° C. The pressure during second stage activation is in the range of between 35 and 200 atmospheres, more preferably, between 50 and 175 atmospheres and most preferably, between 75 and 150 atmospheres.

The duration of second stage activation is the time necessary for the catalyst to be contacted by at least 500,000 liters of activation gas (STP) per kilogram of catalyst, more preferably, at least 1,000,000 liters per kilogram of catalyst and most preferably, 1,500,000 liters per kilogram of catalyst of activation gas. This volume is provided by a space velocity which may range from 1,000 to 20,000 liters (STP) of activation gas per hour per kilogram of catalyst.

The last step in the process of this invention is the synthesis step. In this step, a stream of synthesis gas, having the same composition as the activation gas, is passed over the now activated catalyst. The synthesis gas reactants are catalytically reacted to produce the product of the process of this invention, a mixture which includes saturated aliphatic alcohols having one to nine carbon atoms.

During the synthesis step, the space velocity of the synthesis gas is, like the activation gas, in the range of 1,000 to 20,000 liters (STP) per hour per kilogram of catalyst. Synthesis is conducted in a reactor maintained at a temperature in the range of between 200° and 450° C., more preferably, between 275° and 425° C. and most preferably, between 300° and 400° C. The reactor pressure during the synthesis step is in the range of between 35 and 200 atmospheres, more preferably between 50 and 175 atmospheres and most preferably, between 75 and 150 atmospheres. The synthesis step continues indefinitely until catalytic effectiveness diminishes.

The synthesis step may be characterized by special means to insure completeness of the reaction to produce the product of the process of this invention, a mixture comprising aliphatic saturated alcohols having one to nine carbon atoms. In the first of these recycling of the synthesis gas is employed. That is, upon completion of flow through the reactor, the synthesis gas and the catalyst, neat or in a slurry, as will be explained hereinafter, are separated. The catalyst and unreacted synthesis gas are recycled back to the place of their introduction into the reactor. The product stream including a mixture of aliphatic alcohols is separated and removed as a product of the process of this invention. Fresh synthesis gas may be introduced into the reactor along with the recycle stream. Of course, in the case where a fixed bed reactor is employed little or no separation of catalyst is required. In that case only separation of reacted and unreacted gas need be accomplished.

A second preferred means to aid in improving the degree of conversion is the use of a multistage operation. In this operation two or more stages, each comprising a separate reactor, are provided. Each stage has recycle capability. However, only the activated catalyst is recycled. At the outlet of each stage, i.e., reactor, the synthesis gas is separated into product and unreacted gas streams. The product portion is removed while the unreacted synthesis gas is passed on to the next downstream stage. Each stage is equipped with its own activated catalyst which, as indicated above, is recycled.

The reactor employed in the process of this invention is, in one preferred embodiment, a gas sparged reactor. Such a reactor is one in which a heterogeneous solid-gaseous reaction occurs. Two types of gas sparged reactor are within the contemplation of this invention. The first is a fixed bed reactor, employed in those instances where the catalyst particle size is relatively large. The second gas sparged reactor within the contemplation of this invention is either a fluidized bed or gas-entrained reactor, usually employed in those cases where the catalyst particle size is relatively small.

In another preferred embodiment, the reactor employed in one or more steps of the instant invention is a slurry reactor. A slurry reactor, also known as a conduit reactor, or more descriptively, a tubular reactor, is characterized by the suspension of the catalyst in a liquid dispersant, or slurrying agent.

In the gas sparged reactor, the gas, whether reduction, activation or synthesis, directly contacts the solid catalyst. In the case of the fixed bed reactor, the gas flows over and through a fixed bed of the solid catalyst. In a fluidized bed reaction, the gas stream entrains the solid catalyst particles so that they move in constant motion within the reactor. In the slurry reactor contact is not initially between the gas stream and the solid particles. Rather, first contact is between the liquid slurry, in which the solid catalyst particles are dispersed, and the gas. The gas diffuses through the liquid to contact the catalyst particles.

In the slurry reactor of this invention the slurrying agent is selected from the group consisting of petroleum oil, fuel oil fractions, molten paraffin wax, aromatic oils, silicone oil, liquid tetrafluoroethylene polymer and heavy aliphatic alcohol mixtures containing 10 to 20 carbon atoms. Of these slurrying agents petroleum oil is most preferred.

The petroleum oil contemplated for use in the slurry reactor of this invention is a hydrocarbon mixture of hydrocarbons having 18 to 30 carbon atoms. Such a petroleum oil is furthermore characterized by a typical boiling temperature range, at atmospheric pressure, of 200° to 425° C.

A further characteristic of the slurry reactor in the process of this invention is the choice of cocurrent or countercurrent flow of the gas stream and the catalyst particles dispersed in the slurrying agent. In the case where cocurrent flow is desired the gas and liquid slurry streams enter at the same end of the reactor, whereas when countercurrent contact of the gas and catalyst is desired the two streams enter the reactor at opposite ends.

It is emphasized that the reactor type employed in the first activation stage may or may not be the same as the reactor utilized in the second stage activation and synthesis steps. That is, first stage activation may occur in a fluidized bed, a fixed bed or a slurry reactor independent of the type of reactor employed in second stage activation and synthesis, be it fixed bed, fluidized bed or slurry. However, the same reactor is employed in the second stage activation and synthesis steps.

The product of the process of this invention, as stated above, is a mixture which includes aliphatic alcohols having two to nine carbon atoms, the advantages of which have been discussed hereinabove. However, the process of this invention incorporates an added advantage in that an additional component of the product mixture of this reaction is saturated hydrocarbons having four to nine carbon atoms. Since these saturated hydrocarbons are components of typical gasoline blends, they can be incorporated with the alcoholic component into gasoline blends thus improving the economic return of the process of this invention.

The following examples are given to illustrate the scope and spirit of this invention. Since they are illustrative the invention should not be considered as being limited to them.

EXAMPLE 1

A catalyst comprising metal oxides of copper, zinc, aluminum, potassium and chromium having the following weight composition: 34.2% Cu; 32.9% ZnO; 16.4% $Al_2O_3$; 3.0% K; and 3.3% $Cr_2O_3$ was introduced into a fixed bed reactor. The activation of the catalyst then began by introduction into the reactor of a reducing gas stream consisting essentially of 2% hydrogen and 98% nitrogen, both percentages being by volume, based on the total volume of the reducing gas. The gas stream in the reactor had a space velocity of 800 liters (STP) per hour per kilogram of catalyst. The reactor, originally at ambient temperature, was raised in irregular increments until the temperature in the reactor reached 350° C. Although temperature increase was irregular, the temperature rise never exceeded 25° C. per hour. A pressure of 1.4 atmosphere was maintained throughout this first activation stage.

The activation of the partially activated catalyst was completed in the second activation stage. This was accomplished by placing the catalyst in a fixed bed reactor and subjecting the partially activated catalyst to an activation gas stream comprising hydrogen and carbon monoxide present in a molar ratio of 2.0:1, respectively, and further characterized by a carbon dioxide concentration of 10% by volume and a diluent gas concentration of 5.0% by volume, both based on the total volume of the activation gas. The activation gas stream flowed in the activation reactor at a space velocity of 3,000 liters (STP) per hour per kilogram of catalyst at a temperature of 350° C. and a pressure of 100 atmospheres. Activation continued until 1,500,000 liters (STP) of activation gas passed over the catalyst.

Upon completion of second stage activation, and the completion of catalyst activation, the synthesis stage was immediately started. Synthesis occurred in the same reactor at the same temperature and pressure using a synthesis gas stream having exactly the same composition as the activation gas stream, which passed over the activated catalyst at the same space velocity. The synthesis gas was passed through a single reactor without recycle (single pass). The product fluid stream leaving the reactor was analyzed and average values were determined. It was found that on average 17.5 percent of the carbon monoxide charged into the reactor was converted to aliphatic alcohols and hydrocarbons. Of the products, which were separated from the reactant stream, by condensation at ambient pressure, into liquids, it was determined that of the product stream 27% by weight was methanol, 50% by weight was $C_2$–$C_9$ saturated aliphatic alcohols and the remainder, 23% by weight, was $C_4$–$C_9$ hydrocarbons.

EXAMPLE 2

Example 1 was repeated except that the duration of the second stage activation step, in which the activation gas contacted the catalyst in a fixed bed reactor, comprised the time necessary for 550,000 liters of activation gas (STP) to flow over the catalyst. In addition, there was a minor temperature difference in the second stage activation and synthesis reactor. In this example the temperature was maintained at 355° C. rather than 350° C.

The synthesis gas conversion rate as measured by percentage conversion of carbon monoxide was 18.5%. However, the product stream analysis, although satisfactory, was not as favorable as in Example 1. Methanol comprised 63% by weight, $C_2$–$C_9$ alcohols represented 25% by weight and $C_4$–$C_9$ hydrocarbons provided 12% by weight of the product.

COMPARATIVE EXAMPLE 1

Example 1 was repeated again except that the second stage activation step continued for a period sufficient to permit only 80,000 liters (STP) to flow over the catalyst before synthesis was initiated. Again, a minor temperature variation during second stage activation and synthesis was noted. In this example the second stage activation and synthesis temperature was 352° C. rather than 350° C. in Example 1.

An analysis of the product stream indicated a 13% by weight carbon monoxide conversion and a product stream comprising: 90% by weight methanol, 8% by weight $C_2$–$C_9$ alcohols and 2% by weight $C_4$–$C_9$ hydrocarbons.

This example demonstrates the prior art synthesis processes in which very low yields of higher alcohols are obtainable.

EXAMPLES 3–5

Example 1 was repeated in Examples 3–5 using the same catalyst activated in the same way in the first activation stage. The second stage activation and synthesis steps were again conducted in a fixed bed reactor. However, the composition of the activation and synthesis gas was varied as was the duration of the second stage activation step (as measured in liters of activation gas). Non-consequential differences in second stage activation and synthesis temperature (all runs were run at 350°–355° C.) were also noted. There was also a minor space velocity change (2800 rather than 3000 liter per hr per kg) in Example 4.

The results of the synthesis product are tabulated in the Table, which summarizes all the examples. The reaction conditions of these and all other examples are also included therein. It is noted that no summary of the first activation stage is included in that the conditions, other than the catalyst, were exactly the same in all subsequent examples as they were in Example 1.

EXAMPLES 6 AND 7

Example 1 was repeated in Examples 6 and 7 using the same catalyst activated in the same manner in the first activation stage. However, second stage activation and synthesis occurred in a slurry reactor employing a petroleum oil comprising $C_{18}$–$C_{20}$ hydrocarbons. Again, the composition of the activation and synthesis gas stream of these two runs, although unvarying with each other, was somewhat different than Example 1. The temperature of second stage activation and synthesis was the same. However, the pressure was elevated in Example 6. These and other conditions are summarized in the Table.

The excellent results of the product of these runs are summarized in the Table.

EXAMPLE 8

Example 1 was repeated using a different catalyst system. In this catalyst the copper contributed 34.3%, rather than 34.2% by weight. However, the $Cr_2O_3$ was replaced by $Co_2O_3$ and represented 3.4% rather than 3.3% by weight. A summary of the results of this example which varied in certain respects appears in the Table.

EXAMPLE 9

Example 1 was repeated using a different catalyst system. In this catalyst system an additional metal oxide, manganese oxide, was employed. The catalyst composition is summarized in the Table as is the conditions of second stage activation, synthesis and the resultant product stream obtained.

TABLE

| EXAMPLE NO. | 1 | 2 | CE 1 | 3 | 4 | 5 | 6 | 7 | 8 | 9 |
|---|---|---|---|---|---|---|---|---|---|---|
| CATALYST | A[1] | A | A | A | A | A | A | A | B[2] | C[3] |
| ACTIVATION/SYNTHESIS GAS | | | | | | | | | | |
| $H_2/CO$ Molar Ratio | 2.0 | 2.0 | 2.0 | 0.5 | 1.5 | 2.1 | 2.0 | 2.0 | 2.0 | 2.0 |
| $CO_2$, % by Vol. | 10.0 | 10.0 | 10.0 | 5.8 | 6.1 | 1.9 | 1.3 | 1.3 | 11.0 | 1.6 |
| Diluents, % by Vol. | 5.0 | 5.0 | 5.0 | 5.0 | 5.0 | 5.0 | 5.0 | 5.0 | 5.0 | 5.0 |
| ACTIVATION/SYNTHESIS REACTION | | | | | | | | | | |
| Reaction Type | FB[4] | FB | FB | FB | FB | FB | S[5] | S | FB | FB |
| Temperature, °C. | 350 | 355 | 352 | 353 | 354 | 354 | 350 | 350 | 353 | 354 |
| Pressure, atm. | 100 | 100 | 100 | 100 | 100 | 100 | 170 | 100 | 100 | 100 |

TABLE-continued

| EXAMPLE NO. | 1 | 2 | CE 1 | 3 | 4 | 5 | 6 | 7 | 8 | 9 |
|---|---|---|---|---|---|---|---|---|---|---|
| CATALYST | A[1] | A | A | A | A | A | A | A | B[2] | C[3] |
| Space Velocity, liters (STP)/hr/Kg | 3,000 | 3,000 | 3,000 | 3,000 | 2,800 | 3,000 | 4,200 | 3,000 | 2,900 | 4,500 |
| Activation Duration, liters (STP)/Kg | 1,500,000 | 550,000 | 80,000 | 660,000 | 725,000 | 870,000 | 875,000 | 1,500,000 | 550,000 | 500,000 |
| PRODUCT STREAM | | | | | | | | | | |
| CO Conversion per pass, % | 17.5 | 18.5 | 13 | 8 | 19.5 | 27 | 74 | 28 | 12 | 14 |
| Composition, % by Wt ($H_2O$ Free) | | | | | | | | | | |
| Methanol | 27 | 63 | 90 | 44 | 52 | 43 | 12 | 13 | 64 | 49 |
| $C_2$–$C_9$ Alcohols | 50 | 25 | 8 | 38 | 33 | 33 | 42 | 58 | 23 | 32 |
| $C_4$–$C_9$ Hydrocarbons | 23 | 12 | 2 | 18 | 15 | 24 | 46 | 29 | 13 | 19 |

[1]Catalyst A, by Wt: Cu, 34.2; ZnO, 32.9; $Al_2O_3$, 16.4; K, 3.0; $Cr_2O_3$, 3.3.
[2]Catalyst B, by Wt: Cu, 34.3; ZnO, 32.9; $Al_2O_3$, 16.4; K, 3.0; $Co_2O_3$, 3.4.
[3]Catalyst C, by Wt: Cu, 27.3; ZnO, 33.8; $Al_2O_3$, 13.7; K, 3.1; $Cr_2O_3$, 4.5; MnO, 9.2
[4]FB — Fixed bed, Gas Sparged Reactor
[5]S — Slurry Reactor The above detailed description of preferred embodiments and examples illustrating the scope of this invention will make apparent, to those skilled in the art, other embodiments and examples within the scope and spirit of the instant invention. Therefore, the instant invention should only be limited by the appended claims.

What is claimed is:

1. A process for the synthesis of mixtures including $C_2$–$C_9$ saturated aliphatic alcohols comprising:
    a first stage activation step in which a catalyst comprising the oxides of copper, zinc, aluminum, potassium and one or two additional metals selected from the group consisting of chromium, manganese, cerium, cobalt, thorium and lanthanum is activated by contact with a reducing gas stream comprising hydrogen and at least one inert gas, said reducing gas flowing at a space velocity of up to 5000 liters (STP) per hour per kilogram of catalyst whereby said catalyst is partially activated;
    subjecting said partially activated catalyst to a second state activation step wherein said catalyst is contacted by an activation gas stream comprising hydrogen and carbon monoxide, present in a volume ratio in the range of between 0.5:1 and 4:1, respectively, at a temperature in the range of between 200° and 450° C. and a pressure in the range of between 35 and 200 atmospheres, said activation gas flowing at a space velocity in the range of between 1,000 and 20,000 liters (STP) per hour per kilogram of catalyst, said second stage activation continuing until at least 500,000 liters (STP) of activation gas per kilogram of catalyst contacts said catalyst, whereby said catalyst is fully activated;
    synthesizing a mixture including saturated aliphatic alcohols by contacting a synthesis gas stream comprising hydrogen and carbon monoxide present, respectively, in a volume ratio in the range of between 0.5:1 and 4:1, flowing at a space velocity in the range of between 1,000 and 20,000 liters (STP) with said activated catalyst at a temperature in the range of between 200° and 450° C. and a pressure in the range of between 35 and 200 atmospheres.

2. A process in accordance with claim 1 wherein said saturated aliphatic alcohols in said mixture have four to nine carbon atoms.

3. A process in accordance with claim 2 wherein said mixture comprises saturated hydrocarbons having four to nine carbon atoms.

4. A process in accordance with claim 1 wherein said first stage activation begins at ambient temperature and continues, while said first stage activation temperature increases, at a rate not in excess in 25° C. per hour, until a maximum temperature is reached, said maximum temperature being in the range of between 200° and 450° C.

5. A process in accordance with claim 4 wherein said space velocity of said reducing gas stream is at least 200 liters (STP) per hour per kilogram of catalyst.

6. A process in accordance with claim 4 wherein said reducing gas comprises hydrogen present in a concentration of between 1 and 98 mole percent, based on the total molar concentration of said reducing gas and wherein said inert gases include nitrogen.

7. A process in accordance with claim 4 wherein said pressure of said first activation stage is in the range of between 1 and 15 atmospheres.

8. A process in accordance with claim 4 wherein said hydrogen in said reducing gas is converted in said first stage activation reactor at a rate in the range of between 15 and 95%, per pass through the reactor.

9. A process in accordance with claim 1 wherein both said activation and synthesis gases comprise carbon dioxide present in a concentration in the range of between 0 and 25 percent by volume and exerting a partial pressure of less than 13 atmospheres and diluent gases present in a concentration in the range of between 1 and 15 percent by volume, said percentages based on the total volume of said activation and synthesis gases.

10. A process in accordance with claim 9 wherein said volume ratio of hydrogen to carbon monoxide in said activation and synthesis gases in the range of between 2.0:1 and 2.5:1.

11. A process in accordance with claim 9 wherein said activation and synthesis gases comprise carbon dioxide present in a concentration in the range of between 1 and 5 percent by volume, exerting a partial pressure of less than 5 atmospheres and said diluent gas is present in a concentration of between 0.1 and 2 percent by volume and includes one or more of nitrogen, methane, methanol, ethane, ethanol and propane.

12. A process in accordance with claim 1 wherein said second stage activation step occurs for the period necessary for at least 1,000,000 liters (STP) of said activation gas per kilogram of catalyst to contact said catalyst.

13. A process in accordance with claim 12 wherein said second stage activation step occurs for the period necessary for at least 1,500,000 liters of said activation gas per kilogram of catalyst to contact said catalyst.

14. A process in accordance with claim 1 wherein said catalyst comprises copper, present in a concentration of 18 to 45 percent; zinc, present in a concentration of 24 to 50 percent; aluminum, present in a concentration of 5 to 25 percent; potassium, present in a concentration of 1.4 to 2.1 percent; and said one or two additional metals, present in a total concentration of 2.1 to 2.6 percent, all said percentages by weight, based on the total metal weight of said catalyst.

15. A process in accordance with claim 14 wherein said additional metal constituent in said catalyst is selected from the group consisting of chromium, manganese and combinations of the two.

16. A process in accordance with claim 14 wherein the amount of copper to zinc in said catalyst is in the weight ratio range of between 0.4:1 and 1.9:1.

17. A process in accordance with claim 1 wherein said first activation stage is conducted in a gas sparged reactor.

18. A process in accordance with claim 17 wherein said second activation stage and said synthesis step is conducted in a slurry reactor.

19. A process in accordance with claim 1 wherein said first activation stage is conducted in a slurry reactor.

20. A process in accordance with claim 19 wherein said second activation stage and said synthesis step is conducted in a gas sparged reactor.

21. A process in accordance with claim 1 wherein said first and second stage activation and said synthesis steps all are conducted in a slurry reactor wherein said slurrying agent is selected from the group consisting of a hydrocarbon oil, a fuel oil fraction, a molten paraffin wax, an aromatic oil, a silicone oil, a liquid tetrafluoroethylene polymer and a $C_{10}$–$C_{20}$ aliphatic alcohol mixture.

22. A process in accordance with claim 21 wherein said slurrying agent is hydrocarbon oil, said oil comprising a mixture of hydrocarbons having 18 to 30 carbon atoms and characterized by a boiling temperature range, at atmosphere pressure, of 200° to 425° C.

23. A process in accordance with claim 1 wherein said first activation and second activation stages and said synthesis step all occur in a gas sparged reactor.

24. A process in accordance with claim 23 wherein said gas sparged reactor is fixed bed.

25. A process in accordance with claim 23 wherein said gas sparged reactor is fluidized bed.

* * * * *